(12) United States Patent
O'Connor et al.

(10) Patent No.: US 11,565,039 B2
(45) Date of Patent: Jan. 31, 2023

(54) EVENT DETECTION FOR DRUG DELIVERY SYSTEM

(71) Applicant: INSULET CORPORATION, Acton, MA (US)

(72) Inventors: Jason O'Connor, Acton, MA (US); Joon Bok Lee, Lowell, MA (US); Ian McLaughlin, Groton, MA (US); John D'Arco, Wilmington, MA (US)

(73) Assignee: INSULET CORPORATION, Acton, MA (US)

( * ) Notice: Subject to any disclaimer, the term of this patent is extended or adjusted under 35 U.S.C. 154(b) by 301 days.

(21) Appl. No.: 16/599,729

(22) Filed: Oct. 11, 2019

(65) Prior Publication Data

US 2020/0113515 A1 Apr. 16, 2020

Related U.S. Application Data

(60) Provisional application No. 62/744,229, filed on Oct. 11, 2018.

(51) Int. Cl.
*A61M 5/158* (2006.01)
*A61M 5/142* (2006.01)
(Continued)

(52) U.S. Cl.
CPC ......... *A61M 5/158* (2013.01); *A61B 5/14532* (2013.01); *A61B 5/4839* (2013.01);
(Continued)

(58) Field of Classification Search
CPC . A61B 5/4839; A61B 5/14532; A61B 5/0024; A61B 5/02055; A61B 2562/0219;
(Continued)

(56) References Cited

U.S. PATENT DOCUMENTS

| 303,013 A | 8/1884 | Horton |
| 2,797,149 A | 6/1957 | Skeggs |

(Continued)

FOREIGN PATENT DOCUMENTS

| AU | 2015301146 A1 | 3/2017 |
| CN | 1297140 A | 5/2001 |

(Continued)

OTHER PUBLICATIONS

US 5,954,699 A, 09/1999, Jost et al. (withdrawn)
(Continued)

*Primary Examiner* — James D Ponton
*Assistant Examiner* — Neeraja Gollamudi
(74) *Attorney, Agent, or Firm* — Goodwin Procter LLP

(57) ABSTRACT

A drug delivery device may include an Inertial Measurement Unit (IMU) is provided. The IMU may include an accelerometer, a magnetometer, or a gyroscope. Motion parameters may be detected when the drug delivery device is shipped, being prepared for activation for use, or during use. The IMU may provide data indicative of a rapid deceleration, such as when a package containing the drug delivery device is dropped, or some other physical event experienced by the drug delivery device. The drug delivery device may also include internal or external pressure sensors or a blood glucose sensor that may coordinate with the IMU to provide additional feedback regarding the status of the device or user. A controller of the drug delivery device may generate a response depending on the particular parameters being monitored or may change device operational parameters as a result of detected system events.

9 Claims, 5 Drawing Sheets

(51) Int. Cl.
*A61M 31/00* (2006.01)
*A61B 5/145* (2006.01)
*A61B 5/00* (2006.01)

(52) U.S. Cl.
CPC ...... *A61M 5/14244* (2013.01); *A61M 31/002* (2013.01); *A61B 2562/0219* (2013.01); *A61M 2005/14208* (2013.01); *A61M 2005/14252* (2013.01); *A61M 2005/1585* (2013.01)

(58) Field of Classification Search
CPC .................. A61B 5/6848; A61B 5/685; A61B 2017/00075; A61M 5/14244; A61M 31/002; A61M 2205/18; A61M 2230/201; A61M 2205/502; A61M 2005/14284
See application file for complete search history.

(56) References Cited

U.S. PATENT DOCUMENTS

| | | |
|---|---|---|
| 3,631,847 A | 1/1972 | Hobbs |
| 3,634,039 A | 1/1972 | Brandy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky et al. |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Komerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Grothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |

(56) References Cited

U.S. PATENT DOCUMENTS

| | | |
|---|---|---|
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |

(56) References Cited

U.S. PATENT DOCUMENTS

| | | |
|---|---|---|
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | L. Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodat et al. |
| 2009/0030398 A1 | 1/2009 | Yodat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |

(56) References Cited

U.S. PATENT DOCUMENTS

| | | |
|---|---|---|
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1* | 8/2016 | Despa .................. G08B 21/18 |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1* | 5/2017 | Rioux ............... A61M 5/14248 |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1* | 10/2017 | Marlin ................ A61M 5/3234 |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1* | 7/2018 | Edwards ............... G16H 40/67 |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | OConnor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | OConnor et al. |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 1571582 A2 | 9/2005 |
| EP | 0801578 B1 | 7/2006 |
| EP | 2139382 A1 | 1/2010 |
| EP | 2397181 A1 | 12/2011 |

(56) References Cited

FOREIGN PATENT DOCUMENTS

| | | |
|---|---|---|
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2004 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 04092715 A1 | 10/2004 |
| WO | 2005051170 A2 | 6/2005 |
| WO | 05110601 A1 | 11/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2010053702 A1 | 5/2010 |
| WO | 2010132077 A1 | 11/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2020081393 A1 | 4/2020 |
| WO | 2021011738 A1 | 1/2021 |

OTHER PUBLICATIONS

International Search Report and Written Opinion for the International Patent Application No. PCT/US2020/052125, dated Aug. 12, 2020, 15 pages.
International Search Report and Written Opinion for the International Patent Application No. PCT/US2020/050332, dated Sep. 12, 2020, 12 pages.
European Patent Office, "Notification of Transmittal of the ISR and the Written Opinion of the International Searching Authority, or the Declaration," in PCT Application No. PCT/GB2015/050248, dated Jun. 23, 2015, 12 pages.
Unger, Jeff, et al., "Glucose Control in the Hospitalized Patient," Emerg. Med 36(9):12-18 (2004).
Glucommander FAQ downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Searching Authority, Invitation to Pay Additional Fees, International Application No. PCT/US2006/004929, dated Jul. 27, 2006.
Farkas et al. ""Single-Versus Triple-Lumen Central Catheter-Related Sepsis: A Prospective Randomized Study in a Critically Ill Population"" The American Journal of Medicine September 1992vol. 93 p. 277-282.
Davidson, Paul C., et al., A computer-directed intravenous insulin system shown to be safe, simple,and effective in 120,618 h of operation. Diabetes Care, vol. 28, No. 10, Oct. 2005, pp. 2418-2423.
International Search Report and Written Opinion for the International Patent Application No. PCT/US2021/016283, dated Jun. 2, 2021, 15 pages.
Gorke, A. "Microbial contamination of haemodialysis catheter connections." EDTNA/ERCA journal (English ed.) vol. 31,2 (2005): 79-84. doi:10.1111/j.1755-6686.2005.tb00399.x.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Templeton et al, "Multilumen Central Venous Catheters Increase Risk for Catheter-Related Bloodstream Infection Prospective Surveillance Study" Infection 2008; 36: 322-327.

(56) References Cited

OTHER PUBLICATIONS

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 dated Jul. 16, 2010.

International Search Report and Written Opinion in PCT/US2008/079641 dated Feb. 25, 2009.

Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73,1998.

Berger, "An Enhanced Algorithm for Linear Multivariate Calibration," Analytical Chemistry, vol. 70, No. 3, pp. 623-627, Feb. 1, 1998.

Billman et al.,"Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting" retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.

International Preliminary Report on Patentability for the International Patent Application No. PCT/US2019/053603, dated Apr. 8, 2021, 9 pages.

International Search Report and Written Opinion for the International Patent Application No. PCT/US2019/053603, dated Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

International Search Report and Written Opinion for the InternationalPatent Application No. PCT/US2021/018297, dated May 18, 2021, 18 pages.

An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.

International Search Report and Written Opinion for the International Patent Application No. PCT/US2021/017441, dated May 25, 2021, 12 pages.

International Search Report and Written Opinion for the InternationalPatent Application No. PCT/US2021/017664, dated May 26, 2021, 16 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, dated May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gilbon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, dated May 27, 2021, 16 pages.

International Search Report and Written Opinion for the International Patent Application No. PCT/US2020/065226, dated May 31, 2021, 18 pages.

International Search Report and Written Opinion for the International Patent Application No. PCT/US2021/017659, dated May 31, 2021, 13 pages.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, dated Dec. 13, 2017, 8 pages.

Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, dated May 16, 2017, 12 pages.

International Search Report and Written Opinion for the International Patent Application No. PCT/US2018/018901, dated Aug. 6, 2018, 12 pages.

International Search Report and Written Opinion for International Patent Application No. PCT/US2018/052467, dated Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.

"Read NFC Tags with an iPHone App on iOS 11", GoToTags, Sep. 11, 2017, web <https://gototags.com/blog/read-nfc-tags-with-an-iphone-app-on-ios-11/>. (Year:2017).

(56) References Cited

OTHER PUBLICATIONS

International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
Miontaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Fuzzy control system", Wikipedia, Jan. 10, 2020. URL: https://en.wikipedia.org/w/index.php?title=Fuzzy_control_system&oldid=935091190 Retrieved: May 25, 2021.
International Search Report and Written Opinion for the International Patent Application No. PCT/US2021/022694, dated Jun. 25, 2021, 13 pages.
International Search Report and Written Opinion for International Patent Application No. PCT/US2021/051027, dated Jan. 7, 2022, 16 pages.
International Search Report and Written Opinion for International Patent Application No. PCT/US2021/052372, dated Jan. 26, 2022, 15 pages.
International Search Report and Written Opinion for the International Patent Application No. PCT/US2021/046607, dated Jan. 31, 2022, 20 pages.
International Search Report and Written Opinion for the International Patent Application No. PCT/US2021/055745, dated Feb. 14, 2022, 13 pages.
European Search Report for the European Patent Application No. 21168591.2, dated Oct. 13, 2021, 4 pages.
International Search Report and Written Opinion for the International Patent Application No. PCT/US2021/041954, dated Oct. 25, 2021, 13 pages.
International Search Report and Written Opinion for the International Patent Application No. PCT/US2021/047771, dated Dec. 22, 2021, 11 pages.
International Search Report and Written Opinion for the International Patent Application No. PCT/US2021/052855, dated Dec. 22, 2021, 11 pages.
International Search Report and Written Opinion for the International Patent Application No. PCT/US2022/013470, dated May 6, 2022, 14 pages.
International Search Report and Written Opinion for the International Patent Application No. PCT/US2022/013473, dated May 6, 2022, 13 pages.
International Search Report and Written Opinion for the International Patent Application No. PCT/US2022/019079, dated Jun. 2, 2022, 14 pages.
International Search Report and Written Opinion for the International Patent Application No. PCT/US2022/018453, dated Jun. 2, 2022, 13 pages.
International Search Report and Written Opinion for the International Patent Application No. PCT/US22/018700, dated Jun. 7, 2022, 13 pages.
International Search Report and Written Opinion for the International Patent Application No. PCT/US22/019080, dated Jun. 7, 2022, 14 pages.
International Search Report and Written Opinion for the International Patent Application No. PCT/US22/019664, dated Jun. 7, 2022, 14 pages.
International Search Report and Written Opinion for the International Patent Application No. PCT/US21/060618, dated Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

\* cited by examiner

400

```
┌─────────────────────────────────────────────────────────────┐
│ DETECT MOVEMENT RELATING TO NEEDLE DEPLOYMENT COMPONENT     │  402
└─────────────────────────────────────────────────────────────┘
                            │
                            ▼
┌─────────────────────────────────────────────────────────────┐
│ COMPARE DETECTED MOVEMENT TO MOVEMENT PROFILES              │  404
└─────────────────────────────────────────────────────────────┘
                            │
                            ▼
┌─────────────────────────────────────────────────────────────┐
│ DETERMINE OPERATIONAL MODE OF NEEDLE DEPLOYMENT             │  406
│ COMPONENT BASED ON COMPARISON                               │
└─────────────────────────────────────────────────────────────┘
                            │
                            ▼
┌─────────────────────────────────────────────────────────────┐
│ COMMUNICATE THE DETERMINED OPERATIONAL MODE TO THE USER     │  408
└─────────────────────────────────────────────────────────────┘
                            │
                            ▼
┌─────────────────────────────────────────────────────────────┐
│ ADJUST OPERATIONAL PARAMETERS OF DRUG DELIVERY DEVICE BASED │  410
│ ON DETERMINED OPERATIONAL MODE                              │
└─────────────────────────────────────────────────────────────┘
```

EVENT DETECTION FOR DRUG DELIVERY SYSTEM

CROSS-REFERENCE TO RELATED APPLICATION

This application claims priority to U.S. Provisional Application No. 62/744,229, filed on Oct. 11, 2018, the entire contents of which are incorporated herein by reference.

TECHNICAL FIELD

The examples generally relate to medication delivery. More particularly, examples relate to managing operation of a wearable drug delivery device based on detected system events.

BACKGROUND

Many conventional drug delivery devices fail to include sensors that may determine an operational status of the drug delivery device or status of the user of the drug delivery device. As a result, these conventional drug delivery devices typically place burdensome requirements on the users to assess and confirm proper operation of the devices or a status of the user. Users often find these requirements inconvenient and time-consuming.

Accordingly, there is a need for a drug delivery device that includes sensors for accurately determining the operational status of the device and health status of the user to obviate the need to place burdensome requirements on the user to do so directly.

SUMMARY

A method is disclosed that includes detecting motion of a needle deployment component. The detected motion of the needle deployment component may be compared to a number of movement profiles. An operational mode of the needle deployment component may be determined based on the comparison. A notification indicating the determined operational mode of the needle deployment component may be generated. An input may be received in response to the generated notification. The needle deployment component may be activated based on the received input.

An apparatus is disclosed that includes a storage device, a user interface, a needle deployment component, and a processor. The storage device operable to store a number of movement profiles, the movement profiles storing motion parameters value indicative of motion of a needle deployment component. The processor, at least a portion of which is implemented in circuitry coupled to the storage device and the user interface. The processor operable to perform functions. The functions include detecting motion of the needle deployment component. The processor is operable to compare the detected motion of the needle deployment component to each movement profile of the plurality of movement profiles and determine an operational mode of the needle deployment component based on the comparison. A notification is generated indicating the determined operational mode of the needle deployment component and the generated notification is presented on the user interface. Operational parameters are adjusted based on the determined operational mode of the needle deployment component.

BRIEF DESCRIPTION OF THE DRAWINGS

FIG. 4 illustrates an example of a process for determining an operational state of a drug delivery device.

DETAILED DESCRIPTION

This disclosure presents various systems, components, and methods for detecting events experienced by a drug delivery device worn by a user or events experienced by the user and responding to the detected system events. Each of the systems, components, and methods disclosed herein provides one or more advantages over conventional systems, components, and methods.

An example include a body worn drug delivery device that includes an Inertial Measurement Unit (IMU). The IMU may include the capabilities of an accelerometer, a magnetometer, and/or a gyroscope for detecting various parameters indicative of the working status of the drug delivery device and/or a user wearing the device. The drug delivery device may also include internal or external pressure sensors or a blood glucose sensor that may coordinate with the IMU to provide additional feedback regarding the status of the device or user. The drug delivery device may also include a total insulin delivery sensor that may coordinate with other sensors on the device to provide additional feedback on the operational state of the drug delivery device. The drug device may send a variety of alerts to the user and/or a caregiver depending on the particular parameters being monitored or may change device operational parameters as a result of detected system events. Other examples are disclosed and described.

Figure 1:
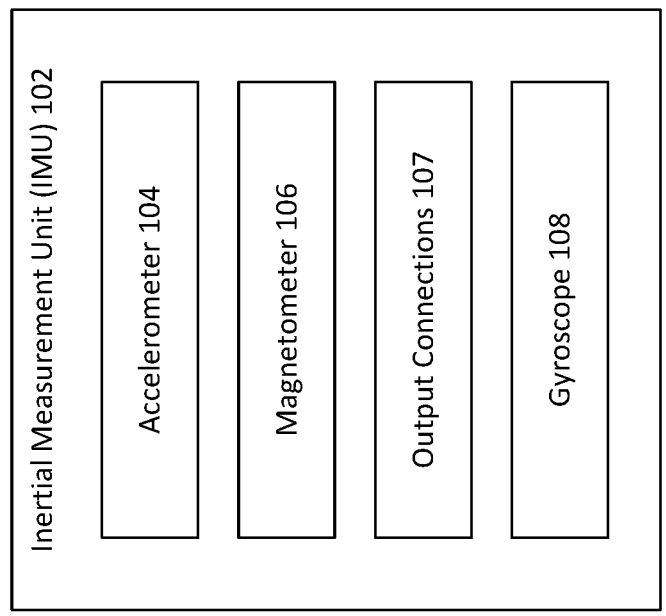
FIG. 1 illustrates an example of an inertial measurement unit (IMU).

FIG. 1 illustrates an example of an inertial measurement unit (IMU) 102. The IMU 102 may include an accelerometer 104, a magnetometer 106, output connections 107 and a gyroscope 108. The IMU 102 may combine the features and capabilities of the accelerometer 104, the magnetometer 106, and the gyroscope 108 for detecting various operational parameters of a device in which the IMU 102 is integrated. In an example, the IMU 102 may be integrated into a drug delivery device such as, for example, a wearable or on-body drug delivery device. Each of the accelerometer 104, the magnetometer 106, and the gyroscope 108 may be coupled to the output connections 107. The output connections 107 may include connections to a controller (shown in another example) or processor for evaluation and additional manipulation or processing as described with reference to other examples.

The accelerometer 104 may generate one or more signals indicative of, for example, a detected or measured acceleration force. The magnetometer 106 may generate one or more signals indicative of, for example, a detected or measured magnetic field. The gyroscope 108 may generate one or more signals indicative of, for example, an orientation of the gyroscope 108, the IMU 102, or a device in which either component is integrated. The signals generated by the accelerometer 104, the magnetometer 106, and the gyroscope 108 may be provided to other components and devices (e.g., a controller or processor) and/or may be stored (e.g., within a non-transitory computer readable memory). In an example, the IMU 102 may detect a motion, a movement, or a position of a device in which it is incorporated (or of a user wearing the device in which the IMU is integrated).

Figure 2:
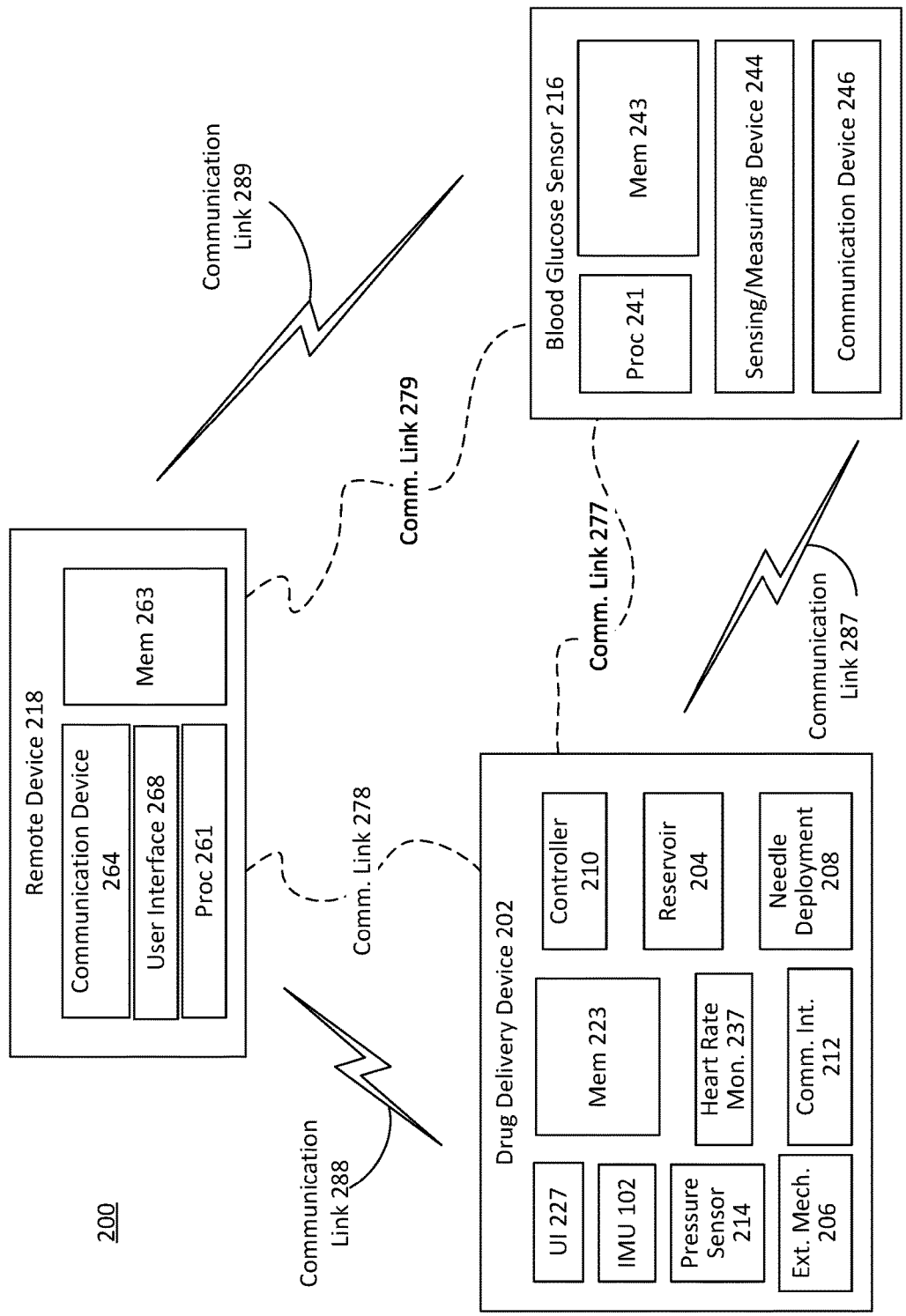
FIG. 2 illustrates an example of a drug delivery device incorporating the example IMU of FIG. 1.

FIG. 2 illustrates an example of a drug delivery system that includes an example of a drug delivery device 202. The drug delivery system 200 may include the drug delivery device 202, a remote device 218 and a blood glucose sensor 216.

The drug delivery device 202 may be a wearable or on-body drug delivery device that is worn by a patient or user on the body of the user. As shown in FIG. 2, the drug delivery device 202 may include the IMU 102, a user interface 227, a pressure sensor 214, an extraction mechanism 206, a memory 223, a heart rate monitor 237, a controller 210, reservoir 204, needle deployment 208, communication device 226. The IMU 102 may be operable to detect of various parameters that may be indicative of the working status (e.g., operational status) of the drug delivery device 202 and/or the health status user of the drug delivery device 202. In an example, the health status of the user of the drug delivery device 202 may include a status of any physical condition of the user including, for example, a motion or position of the user.

In an example, the drug delivery device 202 may also include, or may be coupled to, a number of different sensors (e.g., internal and/or external pressure sensors) that may coordinate with the IMU 102 to provide additional feedback regarding the status of the drug delivery device 202 or the user and/or any events experienced by the drug delivery device 202 or the user (e.g., system events). In an example, the drug delivery device 202 may coordinate with the IMU 102 to send a variety of alerts to the user and/or a caregiver of the user based on any monitored parameter or characteristic of the drug delivery device 202 or detected characteristic of the user (e.g., heart rate or unaffected blood glucose measurement value). In an example, the drug delivery device 202 may coordinate with the IMU 102 to change operational parameters of the drug delivery device 202 based on any monitored parameter or characteristic of the drug delivery device 202 or the user.

The drug delivery device 202 may, for example, also include a heart rate monitor 237 that monitors the user heart rate. The monitored heart rate may be provided to the controller 210, which may use the provided heart rate in the determination of insulin doses or the like.

The wearable drug delivery device 202 may also include a user interface 227. The user interface 227 may include any mechanism for the user to input data to the drug delivery device 202, such as, for example, a button, a knob, a switch, a touch-screen display, or any other user interaction component. The user interface 227 may include any mechanism for the drug delivery device 202 to relay data to the user and may include, for example, a display, a touch-screen display, or any means for providing a visual, audible, or tactile (e.g., vibrational) output (e.g., as an alert). The user interface 227 may also include a number of additional components not specifically shown in FIG. 2 for sake brevity and explanation. For example, the user interface 227 may include a one or more user input or output components for receiving inputs from or providing outputs to a user or a caregiver (e.g., a parent or nurse), a display that outputs a visible alert, a speaker that outputs an audible, or a vibration device that outputs tactile indicators to alert a user or a caregiver of an operational status, a form of notification, or the like.

As shown in FIG. 2, the drug delivery device 202 may include a reservoir 204 configured to store or hold a liquid or fluid. The stored liquid may be any type of drug or therapeutic agent, such as insulin or morphine. In an example, the drug delivery device 202 may be an insulin delivery device and the reservoir 204 may be configured to store insulin. The drug delivery device 202 may further include a drug extraction mechanism or component 206 and a needle deployment mechanism or component 208. The extraction mechanism 206 may extract the liquid drug stored in the reservoir 204. In an example, the extraction mechanism 206 may include a pump or a plunger (not shown).

The needle deployment component 208 may include a needle (not shown) and any other fluid path components, such as a cannula (not shown), for coupling the reservoir 204 containing the stored liquid drug to the user. In an example, the needle deployment component 208 may include a needle (not shown) and a cannula (not shown). The needle may provide initial access to the user (e.g., by piercing a layer of the user's skin) and may then be retracted leaving the cannula coupled to the user. The needle deployment component 208 may include a drive mechanism (not shown) for mechanically driving the needle and the cannula forward toward a user to pierce the skin of the user and to then mechanically retract the needle, leaving the cannula coupled to the user. With the cannula coupled to the user, a fluid path is provided via tubing coupled to the cannula and the reservoir 204.

In an example, the cannula may form a portion of a fluid path component coupling the reservoir 204 to the user. The needle deployment component 208 may be activated to deploy and retract the needle (and cannula) in response to a user input or instruction (e.g., after the drug delivery device 202 is attached or coupled to the user). In an example, the drug delivery device 202 may receive an input, for example, via the communications interface 212, that activates the needle deployment component 208. The needle deployment component is configured, in response to being activated, to provide a fluid path by driving a needle and a cannula (not shown) into the skin of a user and to retract the needle leaving the cannula coupled to the user. After the needle deployment component 208 the fluid path to the user is provided, the extraction mechanism 206 may be operable to expel the stored liquid drug (not shown) from the reservoir 204 to provide the liquid drug to the user via the fluid path. The fluid path may include tubing (not shown) coupling the drug delivery device 202 to the user (e.g., tubing coupling the cannula to the reservoir 204).

The drug delivery device 202 may further include a controller 210 and a communications interface 212. The controller 210 may be implemented in hardware, software, or any combination thereof. The controller 210 may be a processor. The controller 210 may direct operation of the drug delivery device 202. The controller 210 may receive data or information indicative of the operational status of the drug delivery device 202 and/or the status of the user from the IMU 102, as well as from any other sensor of the drug delivery device 202 or sensor coupled thereto.

The controller 210 may process the data from the IMU 102 or any sensor to determine if an alert or other communication is to be issued to the user and/or a caregiver of the user. The controller 210 may process the data from the IMU 102 or any other coupled sensor to determine if an alert or other communication is to be issued to the user and/or a caregiver of the user or if an operational mode of the drug delivery device 202 is to be adjusted. The controller 210 may provide the alert, for example, through the communications interface 212. The communications interface 226 may provide a communications link to one or more management devices physically separated from the drug delivery device 202 including, for example, a remote device 218 of the user and/or a caregiver of the user (e.g., a parent). The controller 210 may provide the alert through the communications interface 212. The communications interface 212 may be operable to provide a communications link to one or more remote devices physically separated from the drug delivery device 202 including, for example, a remote device 218 of the user and/or the caregiver. The communication links (shown as lightning bolts) provided by the communications interface 212 may include any wired or wireless communication link operating according to any known communications protocol or standard, such as Bluetooth®, LTE, 802.11x family, or the like.

In an example, the drug delivery device 202 may include a pressure sensor 214. The pressure sensor 214 may be coupled to the reservoir 204, the extraction mechanism 206, the needle deployment component 208, and/or any portion of the fluid path coupling the reservoir 204 to the user. The pressure sensor 214 may detect pressure and/or pressure changes within of the aforementioned components and/or the fluid path and/or may detect any drive resistance in providing the stored liquid drug to the user. The data and information related to the detected pressure and/or pressure changes provided by the pressure sensor 214 may be used separately or in combination with other data from other sensors by the controller 210 to determine an occlusion in the fluid path, an absorption issue, an insertion site issue, or the like. The controller 210 may use the pressure sensor 214 data or information separately or in combination with other data or information from other sensors, such as the IMU 102 or blood glucose sensor 216, or other devices, such as the remote device 218.

For reference, FIG. 2 further shows the drug delivery device 202 in relation to a glucose monitor 216 such as, for example, a continuous glucose monitor (CGM). The CGM 216 may be physically separate from the drug delivery device 202 or may be an integrated component thereof. The CGM 216 may provide the controller 210 with data indicative of measured or detected blood glucose (BG) levels of the user. The blood glucose sensor 216 or CGM 216 may include a processor 241, a memory 243, a sensing or measuring device 244, and a communication device 246. For example, the processor 241 may be operable to provide blood glucose measurements obtained from the sensing or measuring device 244 to the drug delivery device 202 via the communication device 246. The communication device 246 may exchange signals with the communications interface 212 of the drug delivery device 202 via wired communication link 277 or wireless communication link 287.

FIG. 2 further shows an example of a remote device 218. The remote device 218 may be maintained and operated by the user or the caregiver. The remote device 218 may contain analog and/or digital circuitry that may be implemented as a processor 261 (or controller) for executing processes to manage a user's blood glucose levels and for controlling the delivery of the drug or therapeutic agent to the user. The processor 261 may also be operable to execute programming code stored in the memory 263. For example, the memory 263 may be operable to store an artificial pancreas application (not shown) that may be executed by the processor 261. The communication device 264 may be a receiver, a transmitter, or a transceiver that operates according to one or more radio-frequency protocols. For example, the communication device 264 may include a cellular transceiver and a Bluetooth transceiver that enables the management device 206 to communicate with a data network via the cellular transceiver and with the sensor 204 and the wearable drug delivery device 202. The remote device 218 may control operation of the drug delivery device 202 and/or may be used to review data or other information indicative of an operational status of the drug delivery device 202 or a status of the user via, for example, a user interface 268. The remote device 218 may be used to direct operations of the drug delivery device 202. The remote device 218 may receive alerts, notifications, or other communications from the drug delivery device 202 over any known wired or wireless communications standard or protocol communication links, such as wired communication link 278 or wireless communication link 288. In an example, the remote device 218 may be a dedicated diabetes management controller or may be a smartphone or other consumer electronic device including, for example, a desktop, laptop, or tablet. The remote device 218 may communicate with the blood glucose sensor 216 via communication links, such as wired communication link 278 or wireless communication link 288.

The drug delivery device 202 may include a number of additional components not specifically shown in FIG. 2 for simplicity including, for example, a user input interaction component (e.g., one or more user input features for receiving input from the user or the caregiver), a user output interaction component (e.g., a display or one or more visible, audible, or tactile indicators for providing an output to the user or the caregiver), a power supply (e.g., a battery), and a storage device (e.g., a memory device for storing data or executable instructions implemented by a processor).

In an example, the IMU 102 may measure acceleration, measure changes in velocity, and/or measure changes in a position of the drug delivery device 102 that may be indicative of the drug delivery device 202 being damaged (e.g., dropped or hit) or its connection with the user being compromised, prior to use or during use. In an example, the IMU 102 may monitor and measure these parameters and may provide them to the controller 210. The controller 210 may compare the received data to one or more predetermined thresholds that indicate likely damage to the drug delivery device 202. In another example, the IMU 102 may detect and measure the parameters, may compare the detected data to the one or more predetermined thresholds that indicate likely damage to the drug delivery device 202, and may output an indication to the controller 210 whether one or more of the predetermined thresholds has been exceeded by the detected data.

For example, when data relating to acceleration, velocity, and/or position of the drug delivery device 202 exceeds one or more of the damage thresholds (e.g., a velocity change threshold or an acceleration change threshold, such as an acceleration at or greater than gravity of 9.8 mg/dL followed by a sudden negative acceleration indicating a drop of the pod), the controller 210 may determine that damage to one or more components of the drug delivery device 202 has occurred or has likely occurred. In response to the determination that damage has occurred or may have likely occurred, the controller 210 may provide one or more alerts to the user or the caregiver indicating that the needle deployment component 208 or another component of the drug delivery device 202 may be damaged and/or may not operate properly. In an example, the alert may be provided to a device operated by the user or a caregiver, such as, for example, the remote device 218. In an example, the alert may indicate that the drug delivery device 202 should be discarded and/or replaced.

Figure 3:
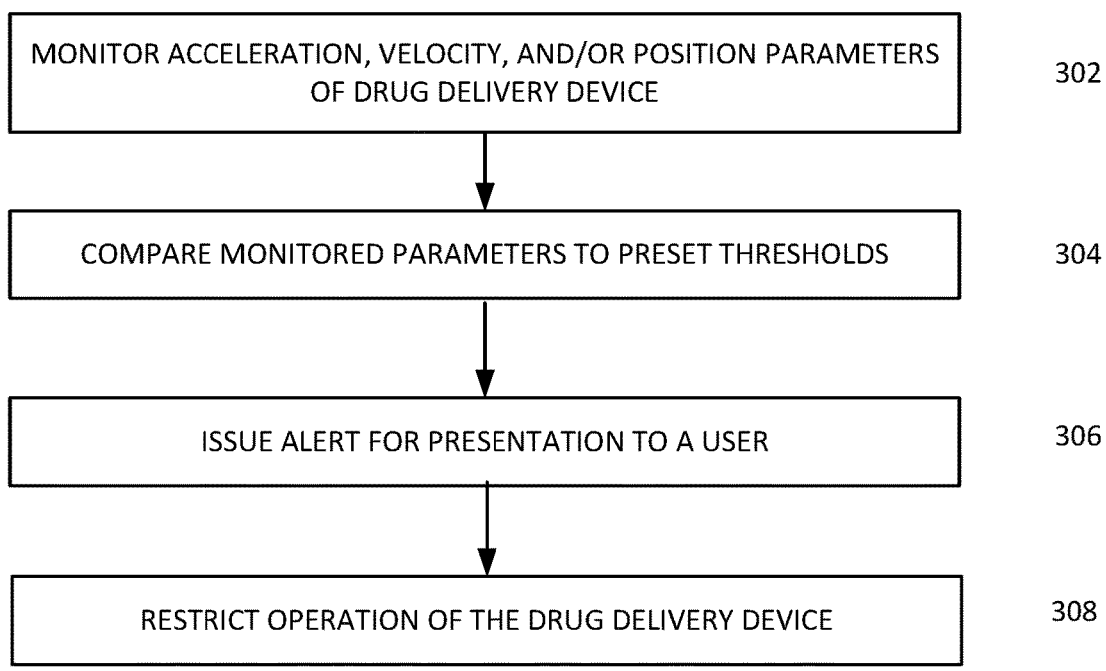
FIG. 3 illustrates an example of process that evaluates motion parameters monitored by the IMU example of FIG. 1.

FIG. 3 illustrates an example of a process 300 for determining that a fault or damage has occurred to a drug delivery device. The illustrated example of the process 300 is described with reference to the system of FIG. 2. In the example of FIG. 3, the process 300 enables the determination that a fault in drug delivery device 202 and/or damage of the drug delivery device 202 has occurred based on parameters monitored by the IMU 102. The occurrence of a fault or damage to the drug delivery device 202 may be determined prior to the drug delivery device 202 being in an activated operational state (i.e., unpackaged and positioned for delivery of a drug to the user) or in a pre-activated operational ready state (i.e., not unpackaged or, if unpackaged, not yet positioned for delivery of a drug to the user, such as either the pod/device is on the body but the needle is not yet injected, or having the pod opened and filled but not yet put on the body).

At 302, one or more parameters that may indicate possible damage to the drug delivery device 202 may be monitored by the IMU 102. The parameters may include an acceleration of or a change in acceleration of the drug delivery device 202, a particular velocity or a change in velocity (derived from data provided by or as provided by the accelerometer 104) of the drug delivery device 202, and/or a position or a change in a position (derived from data provided by or as provided by the gyroscope 108) of the drug delivery device 202, or a change in a magnetic field (derived from data provided by or as provided by the magnetometer 106), or a combination of data or information provided by 104, 106 or 108. The parameters may be detected and/or measured by the IMU 102. The parameters may be monitored by the IMU 102 when the drug delivery device 202 is in the activated state of operation (i.e., unpackaged and positioned for delivery a drug to the user) or the pre-activated state of operation (i.e., not unpackaged or, if unpackages, not yet positioned for delivery of a drug to the user). In an example of determining whether damage has occurred prior to use of the drug delivery device 202, the IMU 102 and/or the controller 221 may be minimally powered so the IMU 102 may obtain and provide movement data to the controller 221 and the controller 221 can store the movement data and/or process the movement data. For example, with reference to FIG. 2, the IMU 102 and a controller 210 of the drug delivery device 202 may be supplied with power from a power supply (not shown) while in a pre-activated mode (e.g., prior to activation of the needle deployment component while in the packaging (during shipping, for example, or before first use)) enabling the accelerometer 104, magnetometer 106, and/or gyroscope 108 of the IMU 102 to provide signals representative of detected parameters related to motion to the controller 210, which the controller 210 is operable to evaluate the detected motion parameters to detect motion of the needle deployment component 208. Alternatively, the IMU 102 may be operable to evaluate the detected motion parameters to detect motion of the needle deployment component 208 after activation of the needle deployment component 208. For example, the IMU 102 components, such as the accelerometer 104, magnetometer 106 and the gyroscope 108, may include memory components and logic circuitry or a processor (not shown) that is operable to execute code to perform calculations and other functions, such as evaluating detected motion parameters with respect to motion thresholds stored in the memory component.

In an example, when the IMU 102 or controller 210 detects motion, the motion may be determined in one or more directions of movement of the needle deployment component 208 relative to three orthogonal reference axes (e.g., X, Y and Z). In addition, the IMU 102 and/or the controller is operable, when detecting motion of the needle deployment component 208, to determine an amount of movement for each of the determined one or more directions of movement. Alternatively, or in addition, when the IMU 102 detects motion and the respective detected motion parameters are provided to the controller 210, the IMU 102 or controller 210 may determine a timing of the detected motion in each of the determined one or more directions of movement, a duration of the detected motion in each of the determined one or more directions of movement, a sequence of the detected motion in each of the one or more directions of movement, or the like.

At 304, the controller 210 or the IMU 102 may be operable to evaluate the detected parameters by, for example, comparing the detected motion-related parameters to predetermined movement parameter thresholds stored in a memory (not shown) coupled to the controller 210. The comparison of detected motion-related parameters (e.g., types of motion that have certain characteristics) of the drug delivery device 202 to the predetermined movement parameter thresholds may be performed by the IMU 102 and/or the controller 210. In an example, the thresholds may be predetermined or pre-set based on an operational status of the drug delivery device 202 and may indicate—for example, when exceeded—that the drug delivery device 202 is damaged, likely damaged, or is likely to not operate properly based on a detected or measured parameter relating to acceleration, velocity, and/or position of the drug delivery device 202 (or any change thereof) that, for example, meets or exceeds one or more of the predetermined thresholds.

For example, the controller 210 or the IMU 102 may be further operable to compare the detected motion of the needle deployment component to a first operational mode profile or movement thresholds to determine an operational mode of the needle deployment component 208. For example, the controller 210 or the IMU 102 may determine that the needle deployment component 208 is operating under a first operational mode. The first operational mode may correspond to an operational state of the needle deployment component 208 in which the needle deployment component 208 is operating properly. Alternatively, or in addition, the controller 210 or the IMU 102 may, for example, be operable to determine that the needle deployment component 208 is operating under a second operational mode that corresponds to an erroneous operational state of the needle deployment component 208.

As an alternative to predetermined thresholds for the motion-related parameters or certain characteristics of types of detected motion, the memory coupled to the controller 210 may be operable to store a number of movement profiles related to different faults or damage to drug delivery device 202 as well as specific components, such as the needle extraction module 208, the needle extraction mechanism 206, the reservoir 204, and the like.

In addition, or alternatively, the controller 210 or the IMU 102 may be operable to compare the motion-related parameters or certain characteristics of types of detected motion of the needle deployment component to an early deployment profile. The early deployment profile may be one of the number of movement profiles stored in the memory. The early deployment profile may include acceleration, velocity and position parameters relating to movement of the needle deployment component prior to attachment of a drug delivery device containing the needle deployment component to a user.

In addition, or alternatively, the controller 210 or the IMU 102 may be operable to compare the detected motion of the needle deployment component to a partial deployment profile, which may be one of the number of movement profiles stored in the memory of the drug delivery device 202. The partial deployment profile may include acceleration, velocity and position parameters relating to movement of the needle deployment component when a needle has not retracted after being inserted into a user.

In addition, or alternatively, the controller 210 or the IMU 102 may be operable to compare the detected motion of the needle deployment component to a partial deployment profile, which may be one of the number of movement profiles stored in the memory of the drug delivery device 202. The partial deployment profile may include acceleration, velocity and position parameters relating to movement of the needle deployment component when a needle has not retracted after being inserted into a user.

In addition, or alternatively, the controller 210 or the IMU 102 may be operable to compare the detected motion of the needle deployment component to a non-deployment profile, which may be one of the number of movement profiles stored in the memory of the drug delivery device 202. The non-deployment profile may include acceleration, velocity and position parameters relating to movement of the needle deployment component when not activating in response to an attempted activation of the needle deployment component.

In addition, or alternatively, the controller 210 or the IMU 102 may be operable to compare the detected motion of the needle deployment component to a full deployment profile, which may be one of the number of movement profiles stored in the memory of the drug delivery device 202. The full deployment profile may include acceleration, velocity and position parameters relating to movement of the needle deployment component when driving a needle and a cannula into the user and then retracting the needle leaving the cannula coupled to the user.

At 306, after determining that one or more detected parameters exceed one or more corresponding predetermined thresholds, as set out in the respective profiles, indicative of damage or improper operation (or a high likelihood thereof), the controller 210 or the IMU 102 may take remedial action. For example, the controller 210 or the IMU 102 may be operable to generate a notification or an alert. An alert may be provided to the user and/or the caregiver through the communications interface 212 and may be provided to a remote device 218 of the user and/or the caregiver. The alert may also include providing a visual, audible, and/or tactile indication through a speaker, vibration device light-emitting diode, or the like (not shown) coupled to the controller 210 of the drug delivery device 202. For example, the alert may indicate the determination that the drug delivery device 202 has likely been damaged and/or may not operate properly, for example, due to being dropped, being hit, slept on, or the like. In an example, the alert may indicate or suggest that the drug delivery device 202 should not be used and/or should be replaced. Alternatively, or in addition, a notification may be generated and output by drug delivery device 202 indicating the determination that the drug delivery device 202 has likely been damaged and/or may not operate properly, for example, due to being dropped, being hit, slept on, or the like. The notification may be transmitted wirelessly to the remote device 218 to be presented to a user or caregiver. The notification may be intended to be presented on the remote device 218 via at least one of a visual, an audible, or a tactile notification.

At 308, the controller 210 may restrict operation of the drug delivery device 202. For example, the controller 210 after issuing an alert or providing a notification for presentation to a user, may, at 308, deactivate or restrict an activated drug delivery device 202 based on a response received via an input device, or due to a lack of a response from an input device. For example, the received input may indicate that the drug delivery device 202 is going to be disposed of within a short time frame (e.g., 1 hour or the like). In response to the received input, the controller 221 may enter a restricted operational mode in which it does not provide any control commands to the extraction mechanism 206 or prevent the system from recommending any changes in the current system settings. In another example, it may have been determined that the drug delivery device 202 was damaged prior to activation. In such a situation, the alert generated by the controller 212 at 306 may have indicated the damaged drug delivery device, and the controller 212 may enter the restricted operational mode and no longer provide control commands to the extraction mechanism 206, the needle deployment component 208, or both.

In an example, the drug delivery device 202 may include a heart rate monitor and/or a skin temperature monitor as part of the IMU 102, controller 210 or another component within the drug delivery device 202 that may be used to confirm (or separately determine) that the drug delivery device 202 or the user has experienced an event the severity of which rendered the needle deployment component 208 inoperable. In an example, data from the heart rate monitor and/or the skin temperature monitor may be used to confirm that the needle deployment component 208 is inoperable and a need to issue an alert to that effect at 306. In this example, if the heart rate monitor and/or the skin temperature monitor indicates values that are out of standard norms of the human body, it may indicate that the needle is actually not deployed in the human tissue.

For some drug delivery devices, no mechanism or component is provided that may determine when the needle of the conventional drug delivery device is deployed—or if the needle or cannula properly deployed and provides a fluid path to the user. As a result, these types of drug delivery devices typically send a message to the user and/or the caregiver approximately 90 minutes after activation requesting that the user and/or the caregiver confirm that this type of drug delivery device is operating properly. For example, a conventional drug delivery device may request the user to confirm that that user's BG levels are within an acceptable range approximately 90 minutes after the conventional drug delivery device is activated. Many users find this request message annoying and inconvenient. Further, using BG levels to confirm proper deployment of the needle may be limited for confirming proper operation of a needle insertion/deployment mechanism as BG levels may be within an acceptable range for any number of reasons even when a needle/cannula did not deploy properly.

The drug delivery device 202 and the IMU 102 described herein provide a more accurate and reliable manner for detecting and confirming proper operation of the drug delivery device 202 including proper deployment of a needle/cannula using the needle deployment component 208. When activated to deploy a needle and a cannula and to then retract only the needle, the needle deployment component 208 may move in a number of directions and may cause the drug delivery device 202 to also move in a number of directions. The IMU 102 may detect and measure the movement of the needle deployment component 208 as well as the drug delivery device 202 and/or any other component thereof. The measured or detected movement may be in any direction (e.g., along each of three orthogonal reference axes commonly referred to as the x, y, and z directions for describing movement in three-dimensions). The movement may be detected according to direction, an amount or amplitude of the movement, a sequence of the movement, when the movement occurs, and the duration of the movement in any direction.

This detected movement may then be compared to one or more stored profiles associated with different activations of the needle deployment component 208. Each profile may vary in terms of the movement, amount of movement, sequence of movement, timing, and duration. By comparing the detected movements of the needle deployment component 208 (and/or any other component of the drug delivery device 202) to the one or more predetermined profiles, a determination may be made if the needle deployment component 208 activated properly and without error or if one or more errors occurred.

In an example, multiple different movement or accelerometer profiles associated with operation of the needle deployment component 208 (e.g., various operational scenarios) may be known and/or stored in a memory for comparison including, for example: (1) an early deployment profile—the IMU 102 may detect movement of the needle deployment component 208 prior to the drug delivery device 202 being attached or coupled to the user; (2) a partial deployment profile—the IMU 102 may detect that a full deployment/insertion of the needle was not completed (e.g., the needle may be inserted but was not fully retracted); (3) a non-deployment profile—the IMU 102 may detect that the needle deployment component 208 did not properly activate to insert and retract a needle; and (4) a full/proper deployment profile—the IMU 102 may detect that the needle deployment component 208 properly activated, and properly inserted and retracted a needle into the user as desired.

Each of these example of profiles may include characteristic features relating to direction of movement, amount of movement, time of movement, sequence of movement, and duration of movement and may vary according to these features. By comparing the detected movement of the needle deployment component 208 (e.g., after activation), the IMU 102 and/or the controller 210 may determine what type of deployment occurred. In this way, a more accurate and reliable approach to determining the operational status of the drug delivery device 202 may be determined.

As disclosed herein, each of the profiles may be associated with a mode of operation of the needle deployment component 208 and/or the drug delivery device 202. Based on the comparison of the detected motion or movement of the needle deployment component 208 by the IMU 102, a determination of the resulting mode of the drug delivery device 202 may be made substantially at the time of attempted or actual activation of the needle deployment component 208. The determined mode may then be communicated or provided to the user or caregiver essentially contemporaneously with the user's attempt to activate the drug delivery device 202. In this way, the user may learn immediately after activation of the needle deployment component 208 if the needle and/or needle deployment component 208 was operated properly or if an error in operation occurred. This obviates the need for the 90 minute checkup message to confirm proper operation relied on by conventional drug delivery devices.

FIG. 4 illustrates an example of a method of operation 400 of an apparatus. The apparatus may be operable to determine an operational state or mode of the needle deployment component 208 based on parameters monitored by the IMU 102. At 402, the IMU 102 may detect and/or measure movement of the needle deployment component 208, the drug delivery device 202, and/or any subcomponent thereof. The IMU 102 may detect and/or measure a direction of movement (e.g., in any direction), an amount of movement in a particular direction (e.g., an amplitude of the movement), a sequence of the detected movement (e.g., an order in which each detected movement occurs), a timing of the movement (e.g., when any particular movement occurs), a duration of the movement (e.g., how long each movement lasts), and what component is moving (e.g., the needle deployment component 208 by direct movement and/or a component coupled to the needle deployment component 208 by indirect/responsive movement). In an example, the IMU 102 may be operable to determine the motion of the needle deployment component and to generate one or more signals indicative of the determined motion of the needle deployment component. The one or more generated signals provided to a processor, such as controller 210. The one or more signals may, for example, be related to one or more of a measure of a direction of movement, an amount of movement in a particular direction, a sequence of the detected movement, a timing of the movement, a duration of the movement, or what component is moving. For example, the IMU may be operable to determine one or more directions of movement of the needle deployment component relative to three orthogonal reference axes. Alternatively, or in addition, the IMU may be operable to determine an amount of movement for each of the determined one or more directions of movement. Alternatively, or in addition, the IMU may be operable to determine a timing for each of the determined one or more directions of movement. Alternatively, or in addition, the IMU may be operable to determine a duration for each of the determined one or more directions of movement. Alternatively, or in addition, the IMU may be operable to determine a sequence of the determined one or more directions of movement.

At 404, the detected parameters from 402 may be compared to one or more movement profiles. The movement profiles may be known (e.g., the motion in particular axes of movement, timing of the particular motion, duration of motion, sequences of motion and the like) and stored and may be associated with a number of events that may be experienced by the needle deployment component 208 including, for example, those described herein: (1) early deployment; (2) partial deployment; (3) no deployment; and (4) full deployment. Each profile may specify a direction of movement, a duration of movement, an amount of movement, a sequence of movement, as well as what component is being profiled. The comparison may be made, for example, by comparing the movement parameters of the profiles to the parameters detected by the IMU 102. In an example, the movement parameters detected by the IMU 102 may be compared to one or more thresholds associated with each of the detected parameters. In a further example, the processor or controller may be operable to compare the detected motion of the needle deployment component to an early deployment profile. In the example, the early deployment profile may be related to movement of the needle deployment component prior to a drug delivery device containing the needle deployment component being attached to the user.

In a further example, the processor may be operable to compare the detected motion of the needle deployment component to a partial deployment profile. In the example, the partial deployment profile may be related to a needle failing to retract after being inserted into the user.

In a further example, the processor may be operable to compare the detected motion of the needle deployment component to a non-deployment profile. In the example, the non-deployment profile may be related to the needle deployment component failing to activate in response to the user attempting to activate the needle deployment component.

In another example, the processor may be operable to compare the detected motion of the needle deployment component to a full deployment profile. In the example, the full deployment profile may be related to the needle deployment component driving a needle and a cannula into the user, retracting the needle, and leaving the cannula coupled to the user.

At 406, an operational mode of the needle deployment component 208 may be determined based on the comparison from step 404 described above. Specifically, the operational mode may be based on a determination as to whether the needle deployment component 208 properly deployed and retracted a needle while leaving a cannula coupled to a user (e.g., movement matched full deployment profile), or if one or more errors occurred during activation of the needle deployment component 208 (e.g., movement matched non-deployment profile). For example, the processor or controller 210 may be operable to determine that the detected motion matches at least one of the movement profiles of: full deployment profile, the non-deployment profile, the early deployment profile, and the partial deployment profile. In an example, the operational profile for a certain mode (e.g., may be selected as the likely operational mode of the needle deployment component 208 based on how similarly the detected parameters from the IMU 102 match the characteristics of the movement profile modes described herein.

In an example, one of a number of different operational modes may be determined. In an example, either a first operational mode or a second operational mode may be determined with the first operational mode relating to proper or desired operation of the needle deployment component 208 and the second operational mode relating to improper or erroneous operation of the needle deployment component 208. In an example, multiple different operational modes may be specified with at least each of the four profiles described above equating to at least one operational mode.

At 408, the determined operational mode of the needle deployment component 208 may be communicated or provided to the user and/or the caregiver. The communication may be provided to the user and/or the caregiver through the communications interface 212 and may be provided to a remote device of the user and/or the caregiver (e.g., the remote device 218). The communication may also include providing a visual, audible, and/or tactile (e.g., vibrational) indication through the drug delivery device 202. The communication may indicate a likely operational mode of the needle deployment component 208 such that the user and/or the caregiver know, essentially at the same time as an attempted activation of the needle deployment component 208, whether the activation was successful and proper or if one or more errors occurred.

At 410, the controller 210 may adjust operational parameters of the drug delivery device based on the determined operation mode of the needle deployment component 208. For example, the controller 210 may set insulin delivery dosages to zero, so that no control commands are provided to the extraction mechanism 206. Alternatively, the controller 210 may modify the maximum delivery dose to a lower or higher value than standard if the needle deployment component is in a high-risk deployment mode, such as being placed in a region with scar tissue which may indicate the need, for example, for a 50% reduction in maximum delivery dose due to increased risk of occlusion, or, for example, a 150% increase in maximum delivery dose due to higher possibility of user not receiving the full insulin dosage required. Other operational parameters may prevent the actuation of the drive system of the needle deployment component 208 or the like.

In an example, the IMU 102 may detect when a user of the drug delivery device 202 is asleep or is awake. Based on such a determination, the drug delivery device 202 may adjust drug delivery and/or may adjust alert levels for notifying the user or the caregiver of certain operational states of the drug delivery device 202 or the user.

In an example, the drug delivery device 202 may include or may be in communication with a CGM, such as the CGM 216. Based on a determination of whether the user is asleep or awake by the IMU 102, the drug delivery device 202 may automatically adjust an insulin delivery rate to the user (e.g., basal insulin delivery) and/or may automatically adjust one or more thresholds (e.g., blood glucose thresholds) at which an alert may be communicated to the user or the caregiver.

In general, the drug delivery device 202 may include multiple insulin delivery rates at which the drug delivery device 202 is capable of providing insulin to the user. One of the rates may be selected based on the determined activity level of the user. As an example, a lower delivery rate may be selected when the user is determined to be asleep. Further, the drug delivery device 202 may include multiple alert settings having associated thresholds that vary with each alert level. One of the alert settings may be selected based on the determined activity level of the user. As an example, a higher threshold (e.g., BG value) may be selected when the user is determined to be asleep. In an example, when the user's glucose variability is very low for an extended period of time, a lower activity level may be detected and may also inform alert settings. For example, data provided from the accelerometer 104 may confirm low activity of the user as suspected based on the user's low glucose variability over a period of time, which may be used to adjust alert settings.

In an example, when it is determined that the user is awake, insulin delivery levels and alert levels may be set in the range of 70-80 mg/dL (for example, such that if blood glucose levels dip below or rise above the range an alert may be issued). Additionally, when it is determined that the user is asleep, insulin delivery levels and alert levels may be set in the range of 90-100 mg/dL (for example, such that if blood glucose levels dip below or rise above the range an alert may be issued). Different notification or alert levels could be set for the caregiver.

In an example, the IMU 102 may detect patterns in the activity of the user. For example, the IMU 102 may determine based on sensed movement when the user is likely asleep, likely awake, and likely awake but inactive (e.g., initially after waking or just prior to sleeping). The controller 210 may correlate typical blood glucose variations for the user with the determined activity levels of the user and may adjust insulin delivery levels and/or alert levels accordingly.

In an example, even when the IMU 102 does not detect that the user is asleep, operational settings of the drug delivery device 202 may be changed to the higher detection and/or alert settings during hours when the user normally sleeps. For automated insulin delivery (e.g., operating as an automatic pancreas), the user's target blood glucose (or setpoint) may be changed automatically based on sleep detection. For open loop basal-bolus therapy, the sleep detection may automatically trigger a different basal rate.

As disclosed herein, the pressure sensor 214 may be coupled to any portion of the fluid path coupling the liquid drug stored in the reservoir 204 to the user. The controller 210 may receive data from the pressure sensor 214 along with data from the IMU 102 and the CGM 216 to detect and/or predict occlusion or absorption issues and to better detect false alarms related thereto. The controller 210 may receive data from these sources and may implement prediction matching algorithms to detect different issues or events that the drug delivery device 202 or the user may be experiencing.

In an example, when the pressure sensor 214 detects drive resistance or increased pressure within any portion of the fluid path, the controller 210 may compare data from the IMU 102 and the CGM 216 to determine if an occlusion has been detected or if another issue is occurring. For example, if blood glucose levels of the user are not as expected (e.g., higher or lower than expected but not yet crossing a threshold triggering an alarm), then early detection of an occlusion or other blockage in absorption may be detected. The controller 210 may process motion data from the IMU 102 to determine if the user is moving and active or is stationary. Blood glucose levels may be determined to not be as expected by the controller 210 based on the amount of insulin that should have been delivered (e.g., blood glucose levels are not decreasing, or are not decreasing at the expected rate).

Upon processing the data from the IMU 102, if the user is determined to be largely stationary and not moving, then the controller 210 may determine that the user may be sitting or lying down in a way that is putting pressure on a portion of the fluid path or tubing connecting the drug delivery device 202 to the user. The controller 210 may then issue a notification to the user regarding the issue and request that the user check the fluid path connection or to move around (e.g., to remove the blockage or kink in the tubing).

Once the IMU 102 detects movement of the user in response to the notification, the controller 210 may determine if data from the pressure sensor 214 indicates a drop in pressure (e.g., data indicating no further occlusion or blockage issue). If pressure appears to be returning to normal operational levels, and blood glucose readings for the user return to more normal operational levels, then the controller 210 may determine that the issue has been resolved and was likely caused by a temporary blockage of the fluid path (e.g., perhaps the user was sitting on the tubing).

Alternatively, if the pressure reading data from the pressure sensor 214 returns to normal operating levels but the blood glucose levels of the user continue to be out of range of normal operation or are trending to be out of range, then the controller 210 may determine that the infusion site of the user may be experiencing a problem. For example, the cannula inserted into the user may be dislodged or otherwise positioned incorrectly (e.g., in a manner that prevents absorption). Under such a scenario, the controller 210 may issue a notification or alarm to the user or the caregiver to check the infusion site to determine if the cannula has become dislodged, the drug delivery device 202 has come detached from the user, or if any drug is leaking from the drug delivery device 202.

Additionally, if the pressure reading data from the pressure sensor 214 does not lower after the IMU 102 detects that the user moves around after the initial notification from the controller 210, then the controller 210 may determine that an occlusion or other blockage is indeed occurring to the fluid path (e.g., internal to the drug delivery device 202). The controller 210 may then issue more a serious notification indicating that a likely blockage is occurring.

In an example, when it is determined the user is likely asleep based on data from the IMU 102 and the controller 210 determines that the user may be positioned on top of tubing coupling the drug delivery device 202 to the user, then the controller 210 may issue a notification or alarm to the user that wakes the user—in order to notify the user to move so as to remove the blockage of the tubing.

By correlating motion data from the IMU 102, pressure data from the pressure sensor 214, and blood glucose levels of the user from the CGM, the controller 210 may more efficiently and reliably detect actual occlusion issues and false alarms related thereto.

Figure 5:
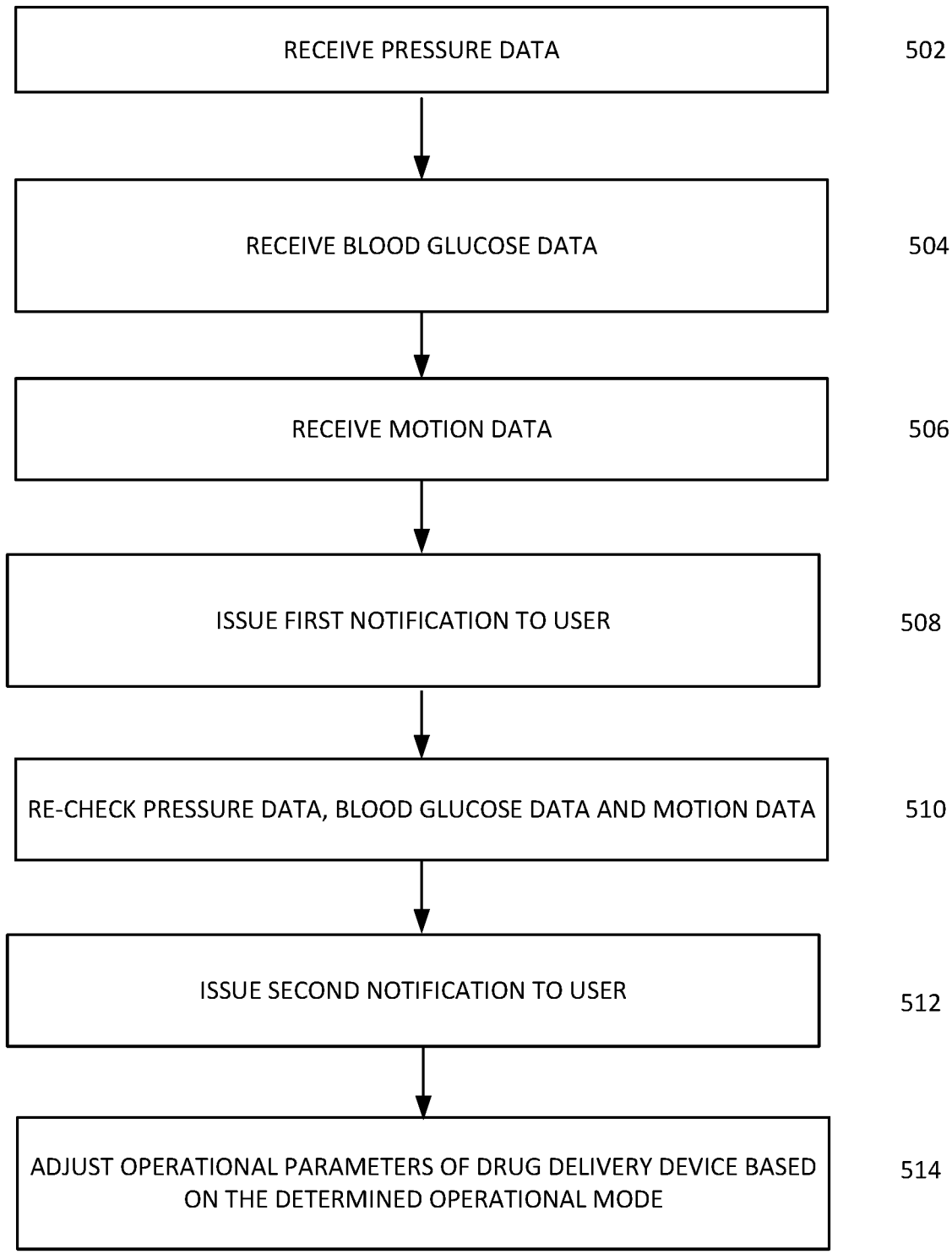
FIG. 5 illustrates an example of another process that determines another operational state of a drug delivery device, such as that illustrated in the example of FIG. 2.

FIG. 5 illustrates an example of a process 500 for more accurately determining an occlusion or absorption issue and distinguishing the same from a false alarm. At 502, the controller 210 may receive pressure data from the pressure sensor 214. For example, the controller 210 may receiving a first signal indicating a pressure of a fluid path coupling a reservoir storing a liquid drug to a user. The pressure sensor 214 may detect any drive resistance or pressure increase within any portion of the fluid path coupled to the user. The pressure sensor 214 may generate one or more signals indicating the same and may provide the signals to the controller 210. Based on the received data and/or signals from the pressure sensor 214, the controller 210 may determine that an abnormal increase in pressure has been detected. In an example, the controller 210 may compare the received data from the pressure sensor to one or more predetermined thresholds.

At 504, the controller 210 may receive BG data from the CGM 216. For example, the controller 210 may receive a second signal indicating a blood glucose level of the user. The CGM 216 may measure or detect BG levels of the user and may generate one or more signals indicating the same. The generated signals may be provided to the controller 210. Based on the received data from the CGM 216, the controller 210 may determine if BG levels are as expected or deviate from a predicted level based on, for example, an amount of insulin that has been delivered to the user. The controller 210 may determine if a severe deviation from expected BG levels is occurring or if BG levels are within an acceptable range. If a severe deviation from expected BG levels is occurring, the controller 210 may issue an immediate notification to the user indicating the same.

If BG levels remain in a tolerable range, then the controller 210 at 506 may receive motion data from the IMU 102. For example, the controller 210 may receive a third signal indicating a motion of the user. Data from the IMU 102 may indicate if the user is in motion or is inactive. In an example described herein, determining a direction of movement may involve determining motion in any three-dimensional direction for example with reference to three orthogonal reference axes commonly referred to as the x, y, and z directions. Accordingly, directions may be along any axes (e.g., in the x axes) and in any direction (e.g., forward or in the positive direction) and directions may be along any combination of axes (e.g., such that a direction is a combination of components along two different axes). Determining an amount of movement may involve determining a distance travelled or an amount of displacement in a particular direction. Determining a timing of a movement may involve determining a time at which movement in a particular direction starts or stops relative to a universal time or relative to motion of other objects or motion in other directions. Determining a duration of movement may involve determining how long movement in a particular direction lasts. Determining a sequence of movement may involve determining an order in which movements in different directions occur. For example, a first direction of movement may be in the negative y direction and subsequently in a positive z direction. Further, determining the movement of an object or component as described herein may further include determining a velocity or acceleration of the object or component.

For example, if the user is inactive, and the BG levels of the user are within an acceptable range, the controller 210 may determine that the user may be sitting, laying (if sleeping), or the like on the tubing connecting the drug delivery device 202 to the user in a manner that blocks or otherwise prevents delivery of the drug to the user.

At 508, the controller 210 may issue a notification to the user based on an evaluation of the first, second, and third signals. The controller 210 upon evaluation of the first, second and third signals, the controller 210 may determine that when the pressure exceeds a first pressure threshold, the blood glucose level is trending outside of a first range, and the motion indicates the user is inactive, the initial notification to comprise an initial alert indicating that tubing connecting a drug delivery device to the user is likely blocked and requesting the user to move to unblock the tubing. For example, the controller 210 may, in response to the evaluation of the received first, second and third signals, issue an initial notification to the user based on the first, second, and third signals. The notification may be provided, as an example, to the remote device 218. The notification may indicate that a blockage in the tubing is suspected and may request that the user check the tubing or otherwise move to adjust the routing of the tubing. In another example, the controller 210 may issue an additional notification. The additional notification may include an additional alert indicating that an occlusion has been detected within the drug delivery device when the pressure continues to exceed the first pressure threshold after the user has moved in response to the initial notification. Alternatively, or in addition, the additional alert may indicate that an infusion site may be dislodged when the pressure drops below the first threshold and the blood glucose level continues trending outside of the first range. Alternatively, or in addition, the additional alert may indicate that an infusion site may be dislodged when the pressure drops below the first threshold and the blood glucose level continues trending outside of the first range. Alternatively, or in addition, the additional alert may indicate proper operation of the drug delivery device when the pressure drops below the first threshold the blood glucose level is trending inside of the first range. The controller 210 may be operable to wirelessly transmit, via the communications interface 212, the initial notification as a message to one or more remote devices, such as remote device 218. Alternatively, or in addition, the initial notification may be provided a visual alert, an audible alert, and/or a vibrational alert from the drug delivery device 202.

At 510, the controller 210 may recheck pressure data from the pressure sensor 214, BG data from the CGM sensor 216, and motion data from the IMU 102. These data may be rechecked after a predetermined period of time after the notification is received by the user and/or the user responds to the notification request. If the pressure data indicates that no blockage or other occlusion is being detected but the BG values are trending out of a desired range, then the controller 210 may determine that an issue with absorption of the drug may be occurring. As a result, at 512, the controller 210 may issue a second notification to the user indicating that an issue with the infusion site may be occurring and may request the user to check for errors at the infusion site or any leakage of the drug.

If the pressure data continues to trend in a manner that indicates pressure is continuing to increase or is not lowering, then the controller 210 may determine that an occlusion issue is occurring, for example internal to the drug delivery device 202. As a result, at 512, the controller 210 may issue a second notification to the user indicating that an occlusion or blockage issue is occurring.

If the pressure data returns to a normal operable range and the BG data returns to a normal operable range, then the controller 210 may determine that the issue related to possible blockage in the tubing has been resolved. Accordingly, the controller 210 may not issue a second notification at 512 or alternatively may issue a notification indicating that the detected problem has been resolved.

In an example, the user may receive an alert from the drug delivery device 202 (e.g., transmitted to and received on the user's smartphone 218 or conveyed by a noise or vibration from the drug delivery device 202). The alert may indicate that a bolus injection of insulin is needed. At times, it may be inconvenient, socially awkward, or physically impossible for the user to access their smartphone or remote control device 218 to send a response signal to confirm the bolus delivery. Under such situations, it may be easier and/or less socially awkward for the user to engage or interact with a user interaction feature or other sensor on the drug delivery device 202 that may be used to confirm the bolus delivery or other action for which confirmation is requested.

In an example, the user may respond to a notification or alert by tapping on the drug delivery device 202. The tapping by the user may be detected by the IMU 102. The tapping that may be registered by the IMU 102 may be determined to indicate acknowledgement or confirmation of the bolus delivery by the user. In an example, the tapping or touching sequence may be set to a specific sequence of tapping, duration, or type of touching (or may be customized) to convey confirmation by the user and to avoid inadvertent confirmation (e.g., through some other alternative or accidental contact with the drug delivery device 202). In an example, the drug delivery device 202 may be programmed by a user or the caregiver to recognize a particular sequence of touching or tapping by the user as indicating confirmation by the user.

In an example, the drug delivery device 202 may include a sensor for detecting a fingerprint of the user (or a fingerprint of the caregiver or other authorized individual) or some other biometric of the user. For example, the fingerprint sensor may be used by the user to register a confirmation to a bolus delivery alert by the controller 210 as described herein.

In response to any confirmation signal from the user, the drug delivery device 202 may indicate through a notification that the command or acknowledgement from the user has been received and the action (e.g., bolus delivery) is being undertaken. In various example, any external sensor or user interface component positioned on the drug delivery device 202 may provide a redundant means for determining the user is inactive and/or asleep.

At 514, the controller 210 may adjust operational parameters of the drug delivery device based on an input received automatically, or in response to the second notification issued to a user. For example, the controller 210 may set insulin delivery dosages to zero, so that no control commands are provided to the extraction mechanism 206 or modify allowable ranges of insulin deliveries to within tighter or looser bounds than normally allowable, such as reducing maximum insulin delivery dosages by the user to approximately 50% of standard settings or increasing maximum delivery dosages by the user to approximately 150% of standard settings. Other operational parameters may prevent the actuation of the drive system of the needle deployment component 208 or the like. Alternatively, the controller 210 may reduce an amount of insulin to be delivered temporarily to ensure that the drug delivery device 202 is operating properly.

In an example, the features and/or functions of the IMU 102 may be implemented by the processor/controller 210. In an example, the IMU 102 may be a separate component from the processor/controller 210. The IMU 102 may be implemented in hardware, software, or any combination thereof.

An example of an apparatus operable to provide the example method 500 of FIG. 5 may be structurally similar to the drug delivery device 202 of FIG. 2. For example, the apparatus include a processor, a storage device, a pressure sensor, a blood glucose sensor, an inertial measurement unit (IMU), and a needle deployment component. In the example, the pressure sensor may be operable to detect pressure in a fluid path between a reservoir storing a liquid drug and cannula configured to couple to a user. The needle deployment component may include the cannula and other components for coupling the cannula to the user. In an example, the pressure sensor may be operable to generate a first signal indictive of a pressure of the fluid path, The blood glucose sensor may be coupled to the user and may be configured to generate a second signal indicative of a blood glucose level of the user. The IMU may be configured to generate a third signal indicative of a motion of the user. The processor may be coupled to the storage device and may be implemented in circuitry operable to perform functions as described herein. The processor may be configured to issue an initial notification for presentation to the user based on the first, second, and third signals. The drug delivery device 202 may include visual, auditory, vibrational components that are operable to provide visible, audible and tactile alerts in response to receipt of the initial notification from the processor.

In an example, the initial notification issued by the processor may include an initial alert indicating that tubing connecting a drug delivery device to the user is likely blocked (i.e., occluded) when the pressure exceeds a first pressure threshold, the blood glucose level is trending outside of a first range, and the motion indicates the user is inactive. The processor may also generate a prompt for receipt by a user requesting that the tubing be unblocked.

In addition, or alternatively, the processor may be operable to issue an additional notification comprising an additional alert indicating that an occlusion has been detected within the drug delivery device when the pressure continues to exceed the first pressure threshold after the user has moved in response to the initial notification.

In addition, or alternatively, the processor may be operable issue an additional notification including an additional alert indicating that an infusion site may be dislodged when the pressure drops below the first threshold and the blood glucose level continues trending outside of the first range.

In addition, or alternatively, the processor may be operable to issue an additional notification including an additional alert indicating proper operation of the drug delivery device when the pressure drops below the first threshold the blood glucose level is trending inside of the first range.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

The invention claimed is:

1. An apparatus, comprising:
 a memory operable to store a plurality of movement profiles of a needle deployment component, wherein the movement profiles comprise parameter values indicative of motion of the needle deployment component;
 a processor, at least a portion of which is implemented in circuitry coupled to the memory; and
 an inertial measurement unit coupled to the processor and having at least one of an accelerometer or a gyroscope, wherein the inertial measurement unit is operable to:
  determine parameters of the motion of the needle deployment component based on signals received from the at least one of the accelerometer or the gyroscope; and
  generate one or more signals indicative of the determined parameters of the motion of the needle deployment component,
 wherein the processor is operable to:
  detect motion of the needle deployment component;
  compare the detected motion of the needle deployment component to each movement profile of the plurality of movement profiles;
  determine an operational mode of the needle deployment component based on the comparison; and
  adjust operational parameters affecting delivery of a liquid drug based on the determined operational mode of the needle deployment component.

2. The apparatus of claim 1, wherein the needle deployment component, upon activation, is configured to drive a needle and a cannula into a user and to retract the needle leaving the cannula coupled to the user.

3. The apparatus of claim 1, wherein the inertial measurement unit is further operable to determine at least one of:
 one or more directions of movement of the needle deployment component relative to three orthogonal reference axes,
 an amount of movement for each of the determined one or more directions of movement,
 a timing for each of the determined one or more directions of movement,
 a duration for each of the determined one or more directions of movement, or
 a sequence of the determined one or more directions of movement.

4. The apparatus of claim 1, wherein the processor is further operable to: compare the detected motion of the needle deployment component to an early deployment profile, wherein the early deployment profile relates to movement of the needle deployment component prior to a drug delivery device containing the needle deployment component being attached to a user.

5. The apparatus of claim 1, wherein the processor is further operable to:
compare the detected motion of the needle deployment component to a partial deployment profile, wherein the partial deployment profile relates to a needle not retracting after being inserted into a user.

6. The apparatus of claim 1, wherein the processor is further operable to:
compare the detected motion of the needle deployment component to a non-deployment profile, wherein the non-deployment profile relates to the needle deployment component not activating in response to an attempted activation of the needle deployment component.

7. The apparatus of claim 1, wherein the processor is further operable to: compare the detected motion of the needle deployment component to a full deployment profile, wherein the full deployment profile relates to the needle deployment component driving a needle and a cannula into a user, retracting the needle, and leaving the cannula coupled to the user.

8. The apparatus of claim 1, wherein the processor is further operable to:
determine the operational mode of the needle deployment component based on determining that the detected motion matches at least one of a full deployment profile, a non-deployment profile, an early deployment profile, or a partial deployment profile of the needle deployment component.

9. The apparatus of claim 1, further comprising:
a user interface, wherein the user interface is operable to:
present a notification indicating the determined operational mode of the needle deployment component.

* * * * *